United States Patent [19]

Klötzer et al.

[11] Patent Number: 4,956,470
[45] Date of Patent: Sep. 11, 1990

[54] 1,3-DISUBSTITUTED/IMIDAZOLIUM SALTS

[75] Inventors: Wilhelm Klötzer, Innsbruck, Austria; Helmut Link, Basel, Switzerland; Renate Müssner, Innsbruck, Austria; Werner Schiestl, Innsbruck, Austria; Nicolas Singewald, Innsbruck, Austria

[73] Assignee: Hoffmann-La Roche Inc., Nutley, N.J.

[21] Appl. No.: 295,165

[22] Filed: Jan. 9, 1989

Related U.S. Application Data

[62] Division of Ser. No. 46,473, May 4, 1987, Pat. No. 4,814,332.

[30] Foreign Application Priority Data

May 13, 1986 [CH] Switzerland .................. 1940/86

[51] Int. Cl.$^5$ ............................................ C07D 413/06
[52] U.S. Cl. .................................... 548/337; 548/326; 548/327; 548/329; 548/336
[58] Field of Search ............... 548/337, 329, 326, 327, 548/336

[56] References Cited

U.S. PATENT DOCUMENTS

| | | | |
|---|---|---|---|
| 3,050,520 | 8/1962 | Erner et al. .................. | 548/335 |
| 4,831,151 | 5/1989 | Link et al. .................. | 514/398 |

FOREIGN PATENT DOCUMENTS

| | | | |
|---|---|---|---|
| 2127355 | 12/1971 | Fed. Rep. of Germany ...... | 548/336 |
| 146595 | 2/1981 | German Democratic Rep. .................. | 548/315 |

OTHER PUBLICATIONS

Karpitschka, Innsbruck, University Dissertation, 1981.
R. Mussner, Innsbruck University Dissertation, 1982.
Synthesis 1982, 592–594, W. Klotzer et al.
Chem. Pharm. Bull. 22, 482–484 (1974), H. Koga et al.
Chemical Abstracts 101 2110040e (1984), Ukhin, L. et al., Zh Obshch. Khim, 1984, 54(7), 1676–8.
Bull. Chem. Soc. of Japan 51, 1846–1855 (1978), C. Yamazaki.
Chem. Ber. 100, 3418–3326 (1967), A. Hetzheim et al.
Chemical Abstracts 102, 59125x (1985), M. Cocco et al., G. Ital. Chemioter, 1984, 31, 33–6.
Tetrahedron Letters 1978, 1295–1298, C. Yamazaki.

Primary Examiner—Mary C. Lee
Assistant Examiner—Catherine S. Kilby Scalzo
Attorney, Agent, or Firm—George M. Gould; Bernard S. Leon; William G. Isgro

[57] ABSTRACT

The imidazolium compounds of the formula

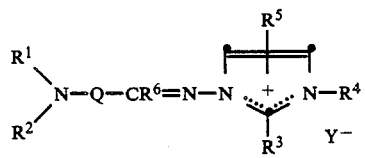

wherein Q is arylene or heteroarylene, the group —NR$^1$R$^2$ is a basic amino group, R$^3$ is lower alkylthio, lower alkoxy or the group —(A)$_n$—Ra, R$^4$ is a saturated or partially unsaturated lower hydrocarbon group, a basic amino group, —N=CRc—Rb, —CHRcRd, —N-H—CHRcRd, —NH—CO—Re or —CH-Rc—CO—Re, R$^5$ is hydrogen, lower alkyl, lower hydroxyalkyl, lower alkoxyalkyl, lower haloalkyl, aryl or a fused benzene ring, R$^6$ is hydrogen or lower alkyl, Ra and Rb independently are aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom, or an aryl, heteroaryl or basic amino group optionally attached via a lower alkyl group, A is vinylene or lower alkylene, n is the integer 0 or 1, the dotted line is an additional double bond and the symbol Y$^-$ is a pharmaceutically acceptable anion, and their pharmaceutically acceptable acid addition salts, which possess valuable pharmacological properties are described. In particular, they possess antibacterial, antimycotic, protozoacidal and/or anthelmintic properties and are especially active against parasitic protozoa and worms. The compounds of formula I can be prepared according to known methods.

3 Claims, No Drawings

1,3-DISUBSTITUTED/IMIDAZOLIUM SALTS

This is a division of application Ser. No. 07/046,473 filed May 4, 1987, now U.S. Pat. No. 4,814,332 issued Mar. 21, 1989.

BRIEF DESCRIPTION OF THE INVENTION

The present invention relates to imidazolium compounds of the formula

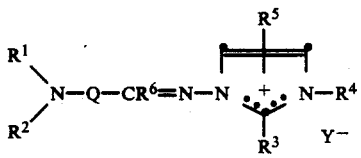

wherein Q is arylene or hetero-arylene, the group $-NR^1R^2$ is a basic amino group, $R^3$ is lower alkylthio, lower alkoxy or the group $-(A)_n-Ra$, $R^4$ is a saturated or partially unsaturated lower hydrocarbon group, a basic amino group or the group $-N=CRc-Rb$, $-CHRcRd$, $-NH-CHRcRd$, $-NH-CO-Re$ or $-CHRc-CO-Re$, $R^5$ is hydrogen, lower alkyl, lower hydroxyalkyl, lower alkoxyalkyl, lower haloalkyl, aryl or a fused benzene ring, $R^6$ is hydrogen or lower alkyl, Ra and Rb independently are aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom, heteroaryl or basic amino group optionally attached via a lower alkyl group, A is vinylene or lower alkylene, n is the integer 0 or 1, the dotted line is an additional double bond and the symbol $Y^-$ is a pharmaceutically acceptable anion, and the pharmaceutically acceptable acid addition salts thereof. The compounds of formula I possess valuable pharmacological properties. In particular, they possess antibacterial, antimycotic, protozoacidal and/or anthelmintic properties.

DETAILED DESCRIPTION OF THE INVENTION

The present invention relates to imidazolium compounds of the formula

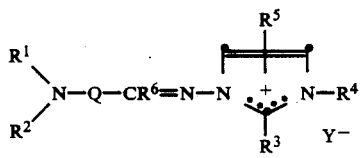

wherein Q is arylene or hetero-arylene, the group $-NR^1R^2$ is a basic amino group, $R^3$ is lower alkylthio, lower alkoxy or the group $-(A)_n-Ra$, $R^4$ is a saturated or partially unsaturated lower hydrocarbon group, a basic amino group or the group $-N=CRc-Rb$, $-CHRcRd$, $-NH-CHRcRd$, $-NH-CO-Re$ or $-CHRc-CO-Re$, $R^5$ is hydrogen, lower alkyl, lower hydroxyalkyl, lower alkoxyalkyl, lower haloalkyl, aryl or a fused benzene ring, $R^6$ is hydrogen or lower alkyl, Ra and Rb independently are aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom, heteroaryl or basic amino group optionally attached via a lower alkyl group, A is vinylene or lower alkylene, n is the integer 0 or 1, the dotted line is an additional double bond and the symbol $Y^-$ is a pharmaceutically acceptable anion, and the pharmaceutically acceptable acid addition salts thereof. The compounds of formula I possess valuable pharmacological properties. In particular, they possess antibacterial, antimycotic, protozoacidal and/or anthelmintic properties.

Objects of the invention are the compounds of formula I and the pharmaceutically acceptable acid addition salts thereof; a process and intermediates for their preparation; the use of the intermediates for the preparation of therapeutically active substances; the compounds of formula I and the pharmaceutically acceptable acid addition salts thereof for use as therapeutically active substances; medicaments based on compounds of formula I and their pharmaceutically acceptable acid addition salts and their preparation; the use of these compounds in the control or prevention of illnesses; as well as the use of the compounds of formula I for the preparation of medicaments useful as antibacterial, antimycotic, protozoocidal and/or anthelmintic agents.

The term "lower", when used together with alkyl, alkoxy or alkylthio; denotes residues and compounds having 1 to 7 carbon atoms, preferably 1 to 4 carbon atoms. The term "alkyl", taken alone or in combinations such as "alkoxy" and "alkylthio", denotes, for example, straight-chain or branched, saturated hydrocarbon residues such as methyl, ethyl, n-propyl, i-propyl, n-butyl, s-butyl, i-butyl, t-butyl and the like.

The term "saturated or partially unsaturated hydrocarbon group" denotes open-chain and cyclic groups and combinations thereof. Examples of saturated and partially unsaturated lower hydrocarbon groups are: lower alkyl groups such as methyl, ethyl, propyl, i-propyl, s-butyl, i-butyl and the like; lower alkenyl groups of 2 to 7 carbon atoms such as 2-propenyl, 2-butenyl, 3-butenyl, 2-methyl-2-propenyl and the like; lower cycloalkyl groups of 3 to 7 carbon atoms optionally substituted by lower alkyl groups such as cyclopropyl, cyclopentyl, 2-methylcyclopentyl, cyclohexyl, 3-methylcyclohexyl and the like; lower cycloalkenyl groups of 3 to 7 carbon atoms optionally substituted by lower alkyl groups such as 3-cyclopentenyl, 1-methyl-3-cyclopentenyl and 3-cyclohexenyl; lower alkyl or alkenyl groups substituted by lower cycloalkyl or cycloalkenyl groups such as cyclopropylmethyl, cyclopropylethyl, cyclopentylmethyl, cyclohexylmethyl, 2-cyclohexenylmethyl and 3-cyclopropyl-2-propenyl. The preferred lower hydrocarbon groups are saturated. The lower alkyl and lower cycloalkyl groups, especially the lower alkyl groups, are particularly preferred lower hydrocarbon groups.

The term "aryl" denotes carbocyclic aromatic groups, preferably mono- or bicyclic groups, for example, phenyl and naphthyl groups, especially phenyl, which may be optionally substituted by one, two or three substituents selected from the group consisting of basic amino, lower alkyl, lower alkoxy, lower alkylthio, lower alkanoyl, lower alkoxycarbonyl, aryl (especially phenyl), halogen, trifluoromethyl, hydroxy, nitro and cyano. These groups are preferably unsubstituted or substituted by one, two or three substitutents from the group consisting of lower alkyl, lower alkoxy, lower alkylthio, halogen, nitro and di(lower alkyl)amino.

The term "arylene" denotes carbocyclic aromatic groups with two free valencies, preferably mono- or bicyclic groups, for example, phenylene and naphthylene groups, especially 1,4- or 1,2-phenylene groups and, in particular, 1,4-phenylene, which can be substituted by one or two substituents selected from the group consisting of lower alkyl, lower alkoxy, lower alkylthio, lower alkanoyl, lower alkoxycarbonyl, aryl (especially phenyl), halogen, trifluoromethyl, hydroxy, nitro and cyano. They are preferably unsubstituted.

The term "heteroaryl" denotes heterocyclic aromatic groups, preferably mono- or bicyclic groups, especially 5- or 6-membered aromatic heterocycles which are optionally fused with a benzene ring and which can be optionally substituted by one, two or three substituents selected from the group consisting of basic amino, lower alkyl, lower alkoxy, lower alkylthio, lower alkanoyl, lower alkoxycarbonyl, aryl (especially phenyl), halogen, trifluoromethyl, hydroxy, nitro and cyano. The 5-membered aromatic heterocycles preferably contain as the hetero ring member(s) an oxygen or sulfur atom or an imino group and optionally in addition one or two nitrogen atoms. The 6-membered aromatic heterocycles preferably contain as the ring member(s) one, two or three nitrogen atoms.

The term "heteroarylene" denotes heterocyclic aromatic groups with two free valencies, preferably mono- or bicyclic groups, especially 5- and 6-membered aromatic heterocycles with two free valencies, which are optionally fused with a benzene ring and which can be substituted by one or two substituents selected from the group consisting of lower alkyl, lower alkoxy, lower alkylthio, lower alkanoyl, lower alkoxycarbonyl, aryl (especially phenyl), halogen, trifluoromethyl, hydroxy, nitro and cyano.

The term "halogen" denotes fluorine, chlorine, bromine and iodine.

The term "basic amino group" or "basic amino" denotes unsubstituted or mono- or disubstituted amino groups having a basic character. The basic amino groups can be represented by the formula —NRR', wherein preferably R is hydrogen or lower alkyl and R' is hydrogen or a saturated or partially unsaturated lower hydrocarbon group which is optionally substituted by one or two lower alkoxy or hydroxy groups or by an amino, lower alkylamino, lower dialkylamino, oxo, lower alkoxycarbonyl or lower alkylenedioxy group or R and R' taken together with the nitrogen atom are a 4- to 7-membered saturated N-heterocycle which is optionally substituted by one or two lower alkyl groups and which can contain as a ring member in place of a methylene group an oxygen or sulfur atom or the group $>SO$, $>SO_2$, $>CO$, $>CH-Rf$ or $>N-Rg$ in which Rf is hydroxy, lower alkanoyl, lower alkoxycarbonyl, carbamoyl, mono- or di(lower alkyl)carbamoyl or a saturated or partially unsaturated lower hydrocarbon group which is optionally attached via an oxygen atom and which is optionally substituted by one or two lower alkoxy or hydroxy groups, or by an amino, lower alkylamino, lower dialkylamino, oxo, lower alkoxycarbonyl or lower alkylenedioxy group and Rg is hydrogen, lower alkanoyl, lower alkoxycarbonyl, carbamoyl, mono- or di(lower alkyl)carbamoyl or a saturated or partially unsaturated lower hydrocarbon group which is optionally substituted by one or two lower alkoxy or hydroxy groups or by an amino, lower alkylamino, lower dialkylamino, oxo, lower alkoxycarbonyl or lower alkylenedioxy group.

Especially preferred basic amino groups characterized by the formula —NRR' are those in which R is hydrogen or lower alkyl and R' is a saturated lower hydrocarbon group or R and R' taken together with the nitrogen atom are a 4-, 5- or 6-membered saturated N-heterocycle which is optionally substituted by hydroxy, lower alkoxy, lower hydroxyalkyl or lower alkoxyalkyl or a 6-membered saturated N-heterocycle which is optionally substituted by one or two lower alkyl groups and which contains in place of a methylene group an oxygen or sulfur atom or an imino or lower alkylimino group.

Particularly preferred basic amino groups characterized by the formula —NRR' are those in which R and R' independently are lower alkyl or taken together with the nitrogen atom are 1-pyrrolidinyl, 1-piperidinyl, 4-morpholinyl, 2,6-dimethyl-4-morpholinyl, 4-thiomorpholinyl or 4-methyl-1-piperazinyl.

If a compound of formula I contains more than one basic amino group, then the groups can be the same or different.

The term "leaving group" preferably denotes a halogen atom such as chlorine, bromine and iodine, lower alkylsulfonyloxy such as methylsulfonyloxy and arylsulfonyloxy such as p-tolysulfonyloxy.

In a preferred embodiment, the invention relates to compounds of formula I above in which $R^3$ is lower alkylthio.

In a further preferred embodiment, the invention relates to compounds of formula I above in which $R^3$ is the groups $-(A)_n-Ra$. Preferably, n is the integer 0 or the integer 1, whereby A preferably is vinylene. In a preferred embodiment, Ra is an unsubstituted phenyl group or a phenyl group substituted by one, two or three substituents from the group consisting of lower alkyl, lower alkoxy, lower alkylthio, halogen, nitro and di(lower alkyl)amino, whereby Ra is, in particular, an unsubstituted phenyl group or phenyl groups monosubstituted by lower alkyl, lower alkoxy or halogen, such as phenyl, p-chlorophenyl, p-tolyl, m-methoxyphenyl and the like. In a still more preferred embodiment, Ra is the group —NRR' in which R and R' independently are hydrogen or lower alkyl or taken together with the nitrogen atom are a 5- or 6-membered saturated heterocycle which is optionally substituted by one or two lower alkyl groups and which contains as the hetero atoms one or two nitrogen atoms or one nitrogen atom and one oxygen or sulfur atom. Preferably, R and R' independently are lower alkyl, especially methyl, or taken together with the nitrogen atom are 4-morpholinyl or 1-piperidinyl.

The $R^5$ preferably is hydrogen.

In a preferred embodiment, $R^4$ is the group $-N=C-R^6-Q-NR^1R^2$.

In a further preferred embodiment, $R^4$ is the group —CHRc—CO—Re in which Rc preferably is hydrogen and Re preferably is lower alkyl, lower alkoxy, an unsubstituted phenyl group or a phenyl group substituted by one, two or three substituents from the group consisting of lower alkyl, lower alkoxy, lower alkylthio, halogen, nitro and di(lower alkyl)amino. More particularly, Re is lower alkyl, especially t-butyl.

Preferably, Q is 1,4-phenylene optionally substituted by one or two substituents from the group consisting of lower alkyl and lower alkoxy. In an especially preferred embodiment, Q is 1,4-phenylene.

Preferably, $R^1$ and $R^2$ independently are lower alkyl. In an especially preferred embodiment, each one of $R^1$ and $R^2$ is methyl.

Preferably, $R^6$ is hydrogen.

The imidazolium salts listed hereinafter are exemplary of the preferred compounds of the class of compounds of characterized by formula I:

1,3-Bis[[p-(dimethylamino)benzylidene]amino]-2-[2-(dimethylamino)vinyl]imidazolium chloride,
1,3-bis[[p-(dimethylamino)benzylidene]amino]-2-[(2-piperidinovinyl)imidazolium chloride,
1,3-bis[[p-(dimethylamino)benzylidene]amino]-2-[(2-morpholinovinyl)imidazolium chloride,
1,3-bis[[p-(dimethylamino)benzylidene]amino]-2-phenylimidazolium chloride,
1,3-bis[[p-(dimethylamino)benzylidene]amino]-2-(p-chlorophenyl)imidazolium chloride,
3-[[p-(dimethylamino)benzylidene[amino[-1-(pivaloylmethyl)-2-(p-tolyl)imidazolium bromide;
3-[[p-(dimethylamino)benzylidene]amino]-1-(pivaloylmethyl)-2-(m-methoxyphenyl)imidazolium bromide and the like.

The compounds of formula I and their pharmaceutically acceptable acid addition salts can be prepared in accordance with the invention by (a) reacting a compound of the formula

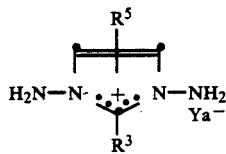 II or

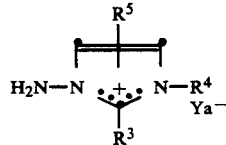 III wherein $R^3$, $R^4$, $R^5$ and the dotted line are as previously described and $Ya^-$ is an anion, with a carbonyl compound of the formula

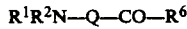 $R^1R^2N-Q-CO-R^6$ IV wherein $R^1$, $R^2$, $R^6$ and Q are as previously described, or (b) reacting a compound of the formula

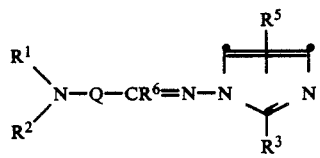 V wherein $R^1$, $R^2$, $R^3$, $R^5$, $R^6$ and Q are as previously described, with a compound of the formula

 $R^{41}-X$ VI wherein $R^{41}$ is a saturated or partially unsaturated lower hydrocarbon group or the group —CHRcRd or —CH-Rc—CO—Re and X is a leaving group, and Rc, Rd and Re are as previously described, or (c) condensing a compound of the formula

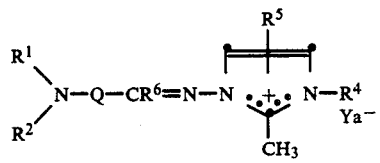 VII wherein $R^1$, $R^2$, $R^4$, $R^5$, $R^6$, Q, $Ya^-$ and the dotted line are as previously described, with an aldehyde of the general formula

 Ra—CHO VIII wherein Ra is as previously described, or (d) reacting a compound of the formula

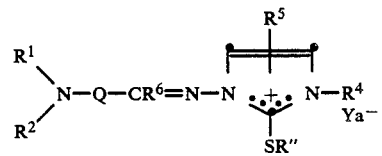 Ib wherein $R^1$, $R^2$, $R^4$, $R^5$, $R^6$, Q, $Ya^-$ and the dotted line are as previously described, and R" is lower alkyl, with ammonia or a primary or secondary basic amine, (e) optionally replacing the anion denoted by $Ya^-$ in a compound obtained by a pharmaceutically acceptable anion and (f) if desired, converting a compound of formula I obtained into a pharmaceutically acceptable salt.

In several of the above processes, in accordance with the invention, it is necessary to block with a protecting group any reactive amino and/or hydroxyl groups in the starting materials. Such cases are readily recognizable by the person skilled in the art and the choice of suitable protecting groups are also known to a person skilled in the art.

The reaction of amines with aldehydes or ketones in accordance with process variant (a) is a reaction which is known and which is familiar to any person skilled in the art. Suitable solvents are, for example, water, lower fatty acids such as acetic acid and propionic acid; lower alcohols such as methanol, ethanol, 1-propanol and 2-propanol; lower fatty acid esters such as ethyl acetate, lower ethers such as diethyl ether, t-butyl methyl ether, ethylene glycol dimethyl ether, tetrahydrofuran and dioxane; halogenated lower hydrocarbons such as methylene chloride, chloroform and ethylene chloride; aromatic hydrocarbons such as benzene, toluene and xylene; acetonitrile; N,N-dimethylformamide and dimethyl sulfoxide. The reaction temperature is not critical. The reaction can be carried out, for example, at a temperature in a range of about 0° C. up to the boiling temperature of the chosen solvent. However, the reaction is preferably carried out at room temperature. In the reaction with the less reactive ketones of formula IV ($R^6$=lower alkyl), a condensation agent such as triethyloxonium tetrafluoro borate is preferably used.

Compounds of formula I in which $R^4$ is a saturated or partially unsaturated lower hydrocarbon group or the group —CHRcRd or —CHRc—CO—Re can be prepared in accordance with process variant (b) by alkylating imidazole derivatives of formula V. This is also a reaction which is known and which is familiar to any person skilled in the art. Suitable solvents are, for example, halogenated lower hydrocarbons such as methylene chloride, chloroform and ethylene chloride; open-chain or cyclic ethers such as diethyl ether, t-butyl methyl ether, ethylene glycol dimethyl ether, tetrahydrofuran and dioxane; lower fatty acid esters such as ethyl acetate; lower alcohols such as methanol, ethanol, 1-propanol and 2-propanol; aromatic hydrocarbons such as benzene, toluene and xylene; acetonitrile; N,N-dimethylformamide and dimethyl sulfoxide. A lower alcohol such as 2-propanol or acetonitrile is preferably used. The reaction temperature is not critical. For example, the reaction can be carried out at a temperature in a range of about 0° C. up to the boiling temperature of the solvent, preferably the temperature is in a range of about room temperature to about 60° C.

Compounds of formula I in which $R^3$ is the group —CH=CH—Ra can be prepared in accordance with process variant (c) by condensing a compound of formula VII with an aldehyde of formula VIII. This is also a reaction which is known and which is familiar to any person skilled in the art. Insofar as Ra is aryl or heteroaryl, the reaction is preferably carried out in the presence of a secondary amine, especially a cyclic amine such as piperidine or morpholine. Suitable solvents are, for example, lower alcohols such as methanol, ethanol, 1-propanol and 2-propanol; aromatic hydrocarbons such as benzene and toluene; open-chain and cyclic ethers such as ethylene glycol dimethyl ether, tetrahydrofuran and dioxane; halogenated lower hydrocarbons such as methylene chloride; N,N-dimethylformamide and dimethyl sulfoxide. The reaction is preferably carried out at the boiling temperature of the chosen solvent. In a preferred embodiment, the solvent used is a water-entrainer, for example an aromatic hydrocarbon or a halogenated lower hydrocarbon, and the water which is formed in the reaction is removed using a water separator.

Insofar as Ra is a basic amino group, the aldehyde of formula VIII is preferably used in the form of a corresponding di(lower alkyl)acetal, whereby the previously mentioned solvents are also suitable for the present case. A lower alcohol such as 1-propanol; a halogenated lower hydrocarbon such as methylene chloride; or dimethylformamide is preferably used as the solvent. The reaction temperature is not critical. The reaction can be carried out at a temperature in a range of about room temperature up to the boiling temperature of the chosen solvent. However, the reaction is preferably carried out at a temperature in a range of about room temperature up to about 100° C.

Compounds of formula I in which $R^3$ is a basic amino group can be prepared in accordance with process variant (d) by reacting a compound of formula Ib with ammonia or a primary or secondary basic amine. This is also a reaction which is known and which is familiar to any person skilled in the art. Suitable solvents are, for example, halogenated lower hydrocarbons such as methylene chloride; open-chain and cyclic ethers such as diethyl ether, t-butyl methyl ether, tetrahydrofuran and dioxane; N,N-dimethylformamide; acetonitrile and dimethyl sulfoxide. N,N-Dimethylformamide and acetonitrile are preferred solvents. The reaction temperature is not critical and the reaction can be carried out, for example, at a temperature from in a range of about 0° C. to the boiling temperature of the chosen solvent. However, the reaction is preferably carried out at room temperature.

The anion denoted by Ya⁻ in a compound obtained can be replaced by a pharmaceutically acceptable anion in accordance with process variant (e). This replacement reaction is also a reaction which is known and which is familiar to any person skilled in the art. Conventional ion-exchangers which are loaded with a pharmaceutically acceptable anion are preferably used.

Compounds of formula I can be converted into pharmaceutically acceptable acid addition salts in accordance with process variant (f). Such acid addition salts can be prepared according to known methods and which are familiar to any person skilled in the art. There come into consideration, not only salts with inorganic acids, but also salts with organic acids, for example hydrochlorides, hydrobromides, sulfates, nitrates, citrates, acetates, maleates, succinates, methanesulfonates, p-toluenesulfonates and the like.

The compounds of formula II which are used as starting materials can be prepared, for example, in accordance with Reaction Scheme I in which $R^3$, $R^5$, Ya⁻ and the dotted line are as previously described:

Reaction Scheme 1

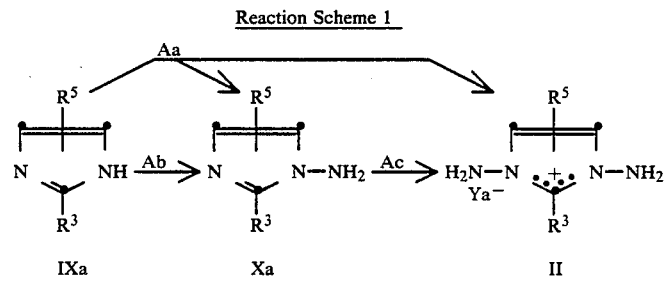

Compounds of formula II in which $R^3$ is lower alkylthio can also be prepared, for example, in accordance with Reaction Scheme II in which $R^5$, R″, Ya⁻ and the dotted line are as previously described and $\phi$ is phenyl:

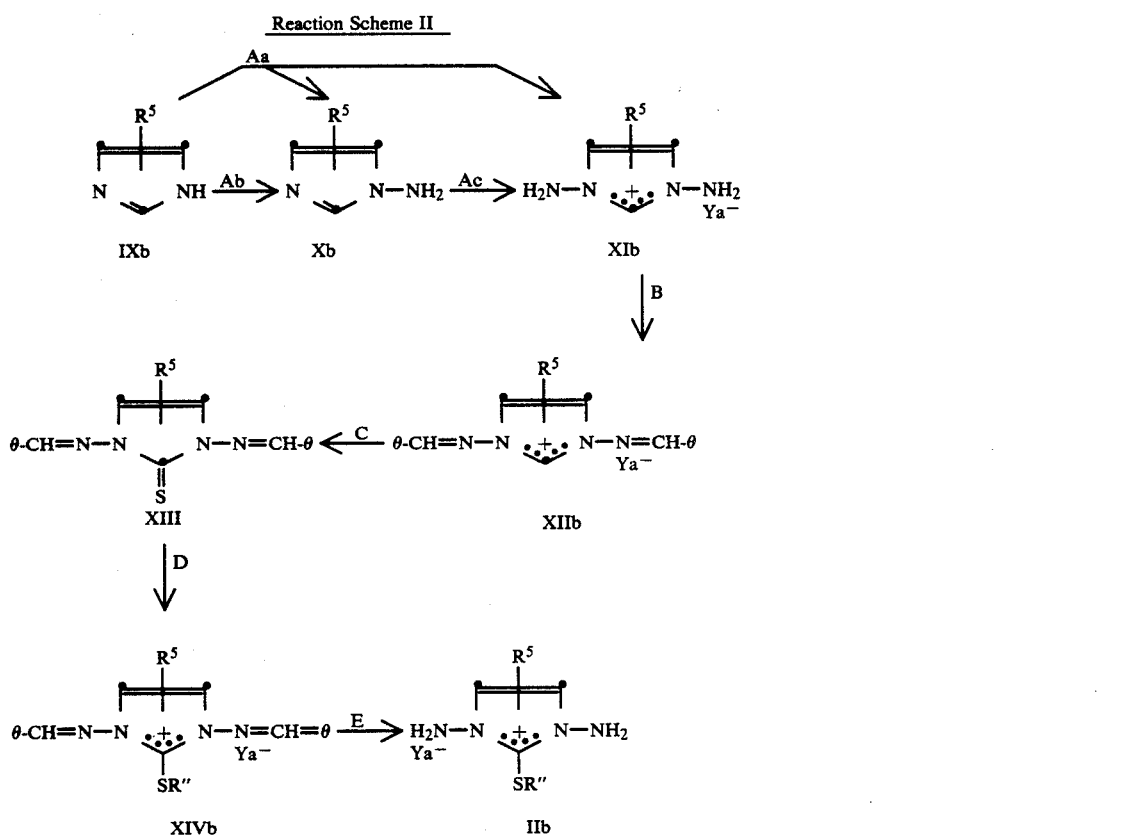
Compounds of formula II in which $R^3$ is the group —CH=CH—Ra can also be prepared, for example, in accordance with Reaction Scheme III in which $R^5$, Ra, $Ya^-$, the dotted line and $\phi$ are as previously described:
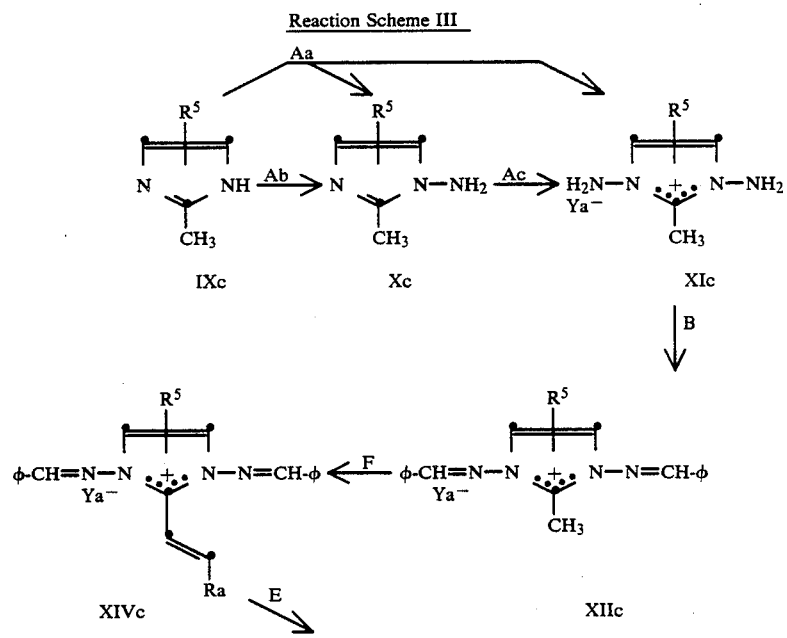

Reaction Scheme III

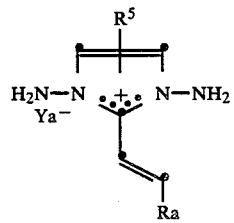

IIc

Compounds of formula II in which $R^3$ is a basic amino group can also be prepared, for example, in accordance with Reaction Scheme IV in which $R^5$, $Ya^-$, the dotted line and $\phi$ are as previously described and $Ra''$ is a basic amino group:

Reaction Scheme IV

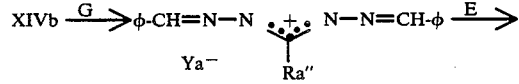

XIVd

-continued
Reaction Scheme IV

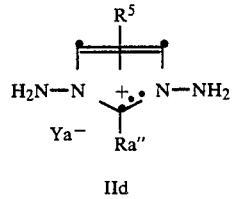

IId

The compounds of formula II in which $R^3$ is the group $-A'-Ra''$, $A'$ is lower alkylene and $Ra''$ is a basic amino group can also be prepared, for example, in accordance with Reaction Scheme V in which $R^5$, $Ra''$, $A'$, $\phi$, $Ya^-$ and the dotted line are as previously described and $X'$ is halogen:

Reaction Scheme V

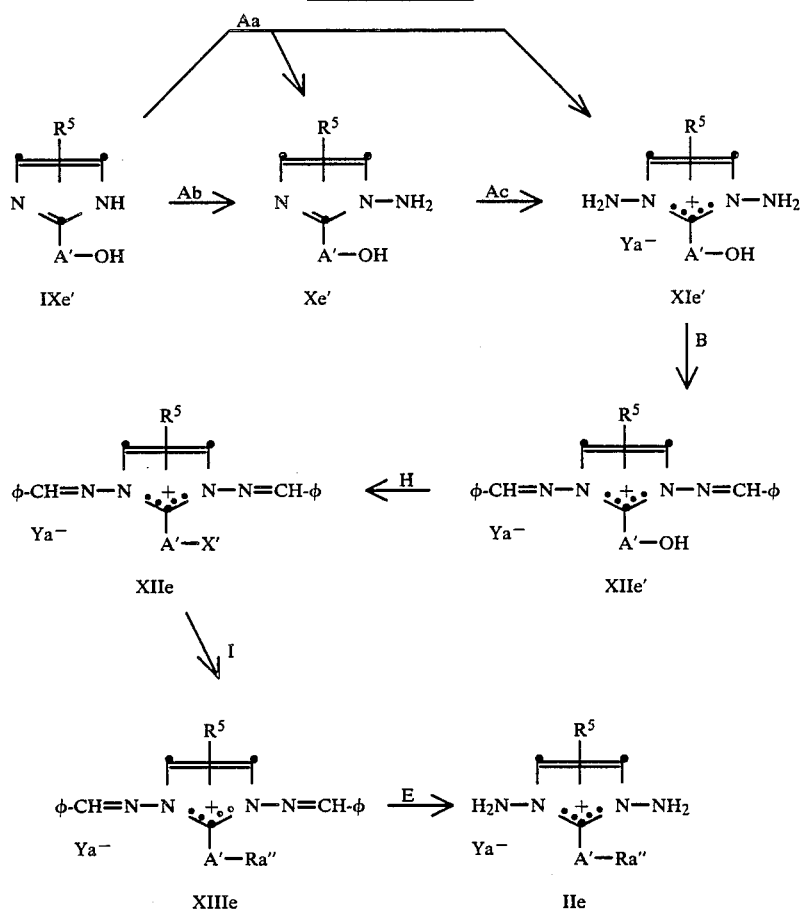

The compounds of formula III can be prepared in accordance with the foregoing Reaction Schemes I–V by using, in each case, as the starting material in place of a compound of formula X, a corresponding compound of the formula

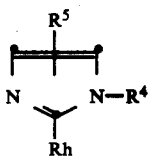

XV wherein Rh is hydrogen, methyl, the group —A′—OH or R³ and A′, R³, R⁴ and R⁵ are as previously described.

The compounds of formula III in which R⁴ is a saturated or partially unsaturated lower hydrocarbon group or the group —CHRcRd or —CHRc—CO—Re can also be prepared, for example, in accordance with the following Reaction Scheme VI in which R³, R⁴¹, R⁵, Ya⁻, φ and the dotted line are as previously described:

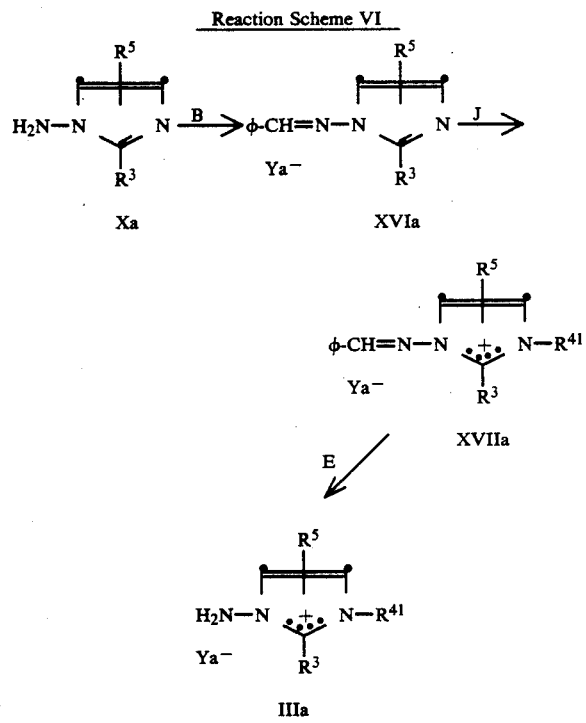

The compounds of formula III in which R⁴ is a saturated or partially unsaturated lower hydrocarbon group or the group —CHRcRd or —CHRc—CO—Re and R³ is the group —SR″, —CH=CH—Ra, Ra″ or —A′—Ra″ can also be prepared by converting a compound of formula Xb, Xc or Xe′ in accordance with the foregoing Reaction Scheme VI, in place of compound Xa, into the compound corresponding to formula XVIIa and further processing this in place of the compounds of formula XII, in accordance with Reaction Schemes II, III, IV and V.

The reaction steps A–G referred to in the Reaction Schemes are explained hereinafter in more detail. In each case the reactions are known and are familiar to any person skilled in the art.

Aa: This reaction step is an electrophilic amination with an aminating agent such as O-(2,4-dinitrophenyl)-hydroxylamine, O-mesitylenesulfonylhydroxylamine or hydroxylamine O-sulfonic acid or its salts with inorganic bases. Preferably, the corresponding alkali metal salts of hydroxylamine O-sulfonic acid, for example, the sodium salt, are used and the reaction is carried out in aqueous solution. In this case, there is generally obtained a mixture consisting of the diamine of formula II or XI and the monoamine of formula X. The two compounds can be separated from each other according to known methods and which are familiar to any person skilled in the art. The Examples which follow contain detailed information concerning the separation of the mixtures obtained.

Ab: This reaction step is an electrophilic amination with an aminating agent such as O-diphenylphosphinylhydroxylamine or O-mesitylenesulfonylhydroxylamine, whereby the starting material is converted with a strong base into an alkali metal salt prior to the reaction with the aminating agent. Suitable bases are, for example, lower alkali metal alkoxides such as sodium methoxide and sodium ethoxide, and alkali metal hydrides such as sodium hydride. Suitable solvents are, for example, N-methylpyrrolidone, N,N-dimethylformamide, lower alcohols, ethers such as tetrahydrofuran, diethylene glycol dimethyl ether, diethylene glycol diethyl ether and diethylene glycol dibutyl ether. The reaction temperature preferably lies in a range of about 0° C. to 100° C. The reaction is preferably carried out at room temperature.

Ac: This reaction step is an electrophilic amination with an aminating agent such as O-diphenylphosphinylhydroxylamine or O-mesitylenesulfonylhydroxylamine. Suitable solvents are, for example, halogenated lower hydrocarbons such as chloroform, methylene chloride and ethylene chloride; ethers such as diethyl ether and tetrahydrofuran; lower alcohols such as ethanol; acetonitrile; N,N-dimethylformamide; dimethyl sulfoxide; and mixtures thereof. The reaction temperature lies in a range of from about 0° C. to the boiling temperature of the chosen solvent. The reaction is preferably carried out at room temperature.

B: In this reaction step, the corresponding starting material is converted into the corresponding aldimine with benzaldehyde. Suitable solvents are, for example, lower fatty acids such as acetic acid and propionic acid; lower alcohols such as methanol, ethanol and 2-propanol; acidic-aqueous media; halogenated lower hydrocarbons such as methylene chloride, chloroform and ethylene chloride; open-chain and cyclic ethers such as diethyl ether, diisopropyl ether, t-butyl methyl ether, ethylene glycol dimethyl ether, diethylene glycol diethyl ether, tetrahydrofuran and dioxane; acetonitrile; N,N-dimethylformamide and dimethyl sulfoxide. The reaction can be carried out of a temperature in the range of from about 0° C. up to the boiling temperature of the chosen solvent. The reaction is preferably carried out at room temperature.

C: The desired thioxo group can be introduced, for example, by treating the starting material with elemental sulfur in the presence of a tertiary amine and in a suitable solvent, for example, in pyridine. The reaction can be carried out at a temperature in a range of from about room temperature to the boiling temperature of the reaction mixture.

D: The desired alkylation can be carried out, for example, by treating the starting material with an alkylating agent such as a tri(lower alkyl)oxonium tetrafluoroborate, for example, with trimethyloxonium tetrafluoroborate. Suitable solvents are, for example, halogenated lower hydrocarbons such as methylene chloride. The reaction is preferably carried out at room temperature.

E: This reaction step comprises the hydrolysis of an aldimine. In a preferred embodiment, the corresponding starting material is treated with an aqueous acid and the aromatic aldehyde obtained is removed by steam distillation. Suitable acids are, for example, dilute hydrochloric acid and dilute hydrobromic acid and tetrafluoroboric acid.

F: In this reaction a compound of formula XIIc is condensed with an aldehyde of formula VIII. When, Ra is aryl or heteroaryl, the reaction is preferably carried out in the presence of a secondary amine, especially a cyclic amine such as piperidine or morpholine. Suitable solvents are, for example, lower alcohols such as methanol, ethanol, 1-propanol and 2-propanol; aromatic hydrocarbons such as benzene and toluene; open-chain and cyclic ethers such as ethylene glycol dimethyl ether, tetrahydrofuran and dioxane; halogenated lower hydrocarbons such as methylene chloride; N,N-dimethylformamide and dimethyl sulfoxide. The reaction is preferably carried out at the boiling temperature of the chosen solvent. In a preferred embodiment the solvent used is a water-entrainer, for example an aromatic hydrocarbon or a halogenated lower hydrocarbon, and the water which is formed in the reaction is removed with a water separator.

Where Ra is a basic amino group, the aldehyde of formula VIII is preferably used in the form of a corresponding di(lower alkyl)acetal, whereby the previously mentioned solvents are also suitable in the present case. A lower alcohol such as 1-propanol; a halogenated lower hydrocarbon such as methylene chloride; or dimethylformamide is preferably used as the solvent. The reaction temperature is not critical. The reaction can be carried out at a temperature in a range of from about room temperature to the boiling temperature of the chosen solvent. However, the reaction is preferably carried out in a range of about room temperature up to about 100° C.

G: In this reaction step, a compound of formula XIVb is reacted with ammonia or a primary or secondary basic amine. Suitable solvents are, for example, halogenated lower hydrocarbons such as methylene chloride; open-chain and cyclic ethers such as diethyl ether, t-butyl methyl ether, tetrahydrofuran and dioxane; N,N-dimethylformamide; acetonitrile and dimethyl sulfoxide. N,N-Dimethylformamide and acetonitrile are preferred solvents. The reaction temperature is not critical and the reaction can be carried out, for example, at a temperature in a range of from about 0° C. up the boiling temperature of the chosen solvent. However, the reaction is preferably carried out at room temperature.

H: In this reaction step, a compound of formula XIIe' is reacted with a halogenating agent such as thionyl chloride and phosphorus oxychloride, whereby excess halogenating agent is preferably used as the solvent. The reaction can be carried out at a temperature range of from about 0° C. to the boiling temperature of the reaction mixture.

I: In this reaction step, a compound of formula XIIe is reacted with ammonia or a primary or secondary basic amine, wherein acetone or N,N-dimethylformamide is preferably used as the solvent. The reaction can be carried out at a temperature range of from about room temperature to the boiling temperature of the reaction mixture.

J: In this reaction step, the corresponding starting material is reacted with a compound of formula VI above. Suitable solvents are, for example, halogenated lower hydrocarbons such as methylene chloride, chloroform and ethylene chloride; open-chain and cyclic ethers such as diethyl ether, diisopropyl ether, ethylene glycol dimethyl ether, diethylene glycol diethyl ether, tetrahydrofuran and dioxane; acetonitrile and N,N-dimethylformamide. This reaction can be carried out at a temperature range of from about 0° C. to the boiling temperature of the chosen solvent.

The compounds of formula V which are used as starting materials can be prepared in analogy to process variant (a) or to reaction step B described above by reacting a compound of formula Xa with an aldehyde or ketone of formula IV.

The compounds of formula VII which are used as starting materials and the starting materials for their preparation can be prepared in analogy to process variants (a) and (b) or in analogy to the processes described for the preparation of the starting materials used in these process variants.

The above-described compounds which are used as starting materials and their use for the preparation of therapeutically active substances of formula I, which have as a common structural feature a group of the formula

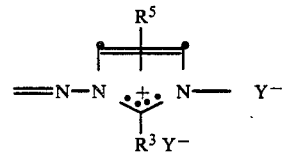

wherein $R^3$, $R^5$ and $Y^-$ have the above significance, also form part of the invention. These are the above-defined compounds of formulas II, III and V.

As mentioned earlier, the compounds of formula I possess valuable pharmacological properties, which render the compounds of formula I particularly useful as antibacterial, antimycotic, protozoacidal and/or anthelmintic agents. By way of further exemplification, the compounds of formula I exhibit antiparasitic properties and are especially active against parasitic protozoa and worms. Their activity against parasitic worms, especially against nematodes such as the filaria, is especially pronounced. These pharmacological properties can be demonstrated by means of test methods which are known and which are familiar to any person skilled in the art.

The filaricidal activity of the compounds of formula I can be determined, for example, on cotton rats (Sigmodon hispidus) which have been infected with Litomosoides carinii. The infection with L. carinii is transmitted by the blood-sucking mite Bdellonyssus bacoti in which the development of the microfilaria in infectious larvae takes place. The cotton rats are infected by exposing them to bites of infected mites. After fourteen (14) weeks, the infected groups of 2–4 animals are treated subcutaneously with the compound to be tested. Forty two (42) days after treatment with the compound to be tested, the experimental animals are dissected, and the adult filaria are removed from the pleural cavity. Living and dead or encapsulated worms are separated from one another and weighed. The filaricidal activity is expressed as the percentage proportion of dead macrofilaria per treatment group. The $ED_{90}$ is then determined by means of Probit analysis using the values from different dosage groups. The $ED_{90}$ is that dosage at which 90% of the worms removed from the pleural cavity are dead. In the following Table, the results which were obtained in the previously described test with representative members of the class of compound defined by formula I are compiled. Moreover, the Table contains data concerning the acute toxicity of some of the compounds of formula I in mg per kg obtained after single oral administration to mice.

TABLE

| Compound | $ED_{90}$ in mg/kg s.c. | $LD_{50}$ in mg/kg p.o. |
|---|---|---|
| A | 1.0 | 312–625 |
| B | 2.0 | — |
| C | 0.55 | — |
| D | <1.0 | 1250–2500 |

Compound A = 1,3-Bis[[p-(dimethylamino)benzylidene]-amino]-2-[2-(dimethylamino)vinyl]imidazolium chloride.
Compound B = 1,3-Bis[[p-(dimethylamino)benzylidene]-amino]-2-(2-piperidinovinyl)imidazolium chloride.
Compound C = 1,3-Bis[[p-(dimethylamino)benzylidene]-amino]-2-(2-morpholinovinyl)imidazolium chloride.
Compound D = 1,3-Bis[[p-(dimethylamino)benzylidene]-amino]-2-phenylimidazolium chloride.

The compounds of formula I can be used as medicaments, for example, in the form of pharmaceutical preparations for enteral or parental administration. The compounds of formula I can be administered, perorally, for example, in the form of tablets, coated tablets, dragees, hard and soft gelatine capsules, solutions, emulsions or suspensions; rectally, for example, in the form of suppositories; or parenterally, for example, in the form of injection solutions.

The preparation of the pharmaceutical preparations can be carried in a manner which is familiar to any person skilled in the art by bringing the substances in accordance with the invention, optionally in combination with other therapeutically valuable substances, into a galenical form together with suitable, non-toxic, inert, therapeutically compatible solid or liquid carrier materials and, if desired, the usual pharmaceutical adjuvants.

Suitable carrier materials include not only inorganic carrier materials, but also organic carrier materials. Thus, for tablets, coated tablets, dragees and hard gelatine capsules there can be used as carrier materials, for example, lactose, maize starch or derivatives thereof, talc, stearic acid or its salts. Suitable carriers for soft gelatine capsules are, for example, vegetable oils, waxes, fats and semi-solid and liquid polyols. Depending on the nature of the active substance, no carriers are, however, required in the case of soft gelatine capsules. Suitable carrier materials for the preparation of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants, the usual stabilizing, preserving, wetting and emulsifying agents, flavor-improving agents, salts for varying the osmotic pressure, buffer substances, solubilizers, coloring and coating agents and antioxidants, can be used.

The dosage at which the compounds of formula I are administered can vary within wide limits depending on the disease to be treated, the age and the individual condition of the warm-blooded host requiring treatment and on the mode of administration and will, of course, be adjusted to the individual requirements in each particular case. For the prophylactic and therapeutic use of the compounds of formula in the treatment of infectious diseases which are caused by bacteria, fungi or parasites, the compounds of formula I are administered to adult patients at a daily dosage of about 0.01 g to about 4 g, especially from about 0.05 g to about 2 g. Depending on the dosage, it is convenient to administer the daily dosage in several unit doses.

The pharmaceutical preparations in accordance with the invention conveniently contain from about 10–1000 mg, preferably 50–500 mg, of a compound of formula I in accordance with the invention.

The Examples which follow further, illustrate the invention. All temperatures are given in degrees Celsius.

EXAMPLE 1

(a) A solution, of 10 g of hydroxylamine O-sulfonic acid prepared at 0°, and 7.4 g of sodium hydrogen carbonate in 60 ml of water is added dropwise to a solution of 7.26 g of 2-methylimidazole in 30 ml of water. The temperature thereby rises to 35°. After stirring for 16 hours, the mixture is acidified with 26 ml of 2N hydrochloric acid. A solution of 6.26 g of benzaldehyde in 20 ml of ether is added thereto, whereupon the mixture is stirred for an additional 6 hours. The precipitated product is filtered and recrystallized from methanol/ether. There is obtained 1,3-bis(benzylideneamino)-2-methylimidazolium benzaldoxime O-sulfonate of melting point 249°–250°. The acidic filtrate obtained is processed in accordance with Example 2a.

(b) 19.2 g of 1,3-bis(benzylideneamino)-2-methylimidazolium benzaldoxime O-sulfonate in 100 ml of water and 70 ml of 2N hydrochloric acid are subjected to a steam distillation until benzaldehyde no longer results. The mixture is evaporated and the residue is placed on a column loaded with 200 ml of ion-exchanger Amberlite IRA 400 (chloride). The column is eluted with about 1 liter of water. The eluate is evaporated and the material obtained is recrystallized from ethanol/methylene chloride. There is obtained 1,3-diamino-2-methyl-imidazolium chloride of melting point 225°–227°.

(c) 0.22 of 1,3-diamino-2-methylimidazolium chloride is dissolved in 5 ml of glacial acetic acid, whereupon the solution is treated with a solution of 0.45 g of 4-dimethylaminobenzaldehyde in 5 ml of glacial acetic acid. After stirring for 2 hours, the yellow precipitate is removed by filtration. After drying, there is obtained 1,3-bis[[p-(dimethylamino)benzylidene]amino]-2-methylimidazolium chloride of decomposition point 264°–266°. The mother liquor is treated with ether, to yield a second portion of the desired product. The material obtained is recrystallized from hot water. There is obtained 1,3-bis[[p-(dimethylamino)benzylidene]amino]2-methylimidazolium chloride of decomposition point 270°.

(d) 0.82 g of 1,3-bis[[p-(dimethylamino)-benzylidene]amino]-2-methylimidazolium chloride is suspended in 30 ml of ethanol, whereupon the suspension is treated with 0.3 g of 4-dimethylaminobenzaldehyde and 0.17 g of piperidine and heated to boiling under reflux.

A deep red solution results. After 20 hours it is left to cool. The precipitated product is removed by filtration and re-precipitated from methylene chloride/ether. After recrystallization from toluene there is obtained 1.3-bis[[p-(dimethyl-amino)benzylidene]amino]-2-[p-(dimethylamino)styryl]imidazolium chloride as a red solid of melting point 238°–240°.

EXAMPLE 2

(a) The acidic filtrate from Example 1a is extracted three times with 15 ml of ether each time. The aqueous phase is neutralized with 9 ml of 4N sodium hydroxide solution while cooling. The precipitate is removed by filtration and re-precipitated from methanol/ether. There is obtained 1-(benzylideneamino)-2-methylimidazole of melting point 122°–124°.

(b) 0.92 g of 1-(benzylideneamino)-2-methylimidazole is dissolved in 10 ml of absolute dichloromethane and then treated with 0.74 g of trimethyloxonium tetrafluoroborate. The mixture is stirred at room temperature overnight and the resulting precipitate is filtered under suction and washed twice with dichloromethane. After reprecipitation from acetonitrile/diethyl ether, there is obtained colorless 1-(benzylideneamino)-2,3-dimethylimidazolium tetrafluoroborate of m.p. 213°–216°.

(c) 0.86 g of 1-benzylideneamino-2,3-dimethylimidazolium tetrafluoroborate is suspended in 30 ml of water. The suspension is treated with 1 ml of 50 percent tetrafluoroboric acid and steam-distilled until benzaldehyde no longer passes over. The colorless acidic solution is then treated with 0.45 g of p-(dimethylamino)benzaldehyde and stirred at room temperature for 3 hours. The resulting orange-yellow precipitate is removed by filtration under suction, washed three times with water and three times with diethyl ether and recrystallized from methanol/ethanol. There is obtained 1-[[p-(dimethylamino)benzylidene[amino[-2,3-dimethylimidazolium tetrafluoroborate in the form of yellow needles with a melting point of 248°–251°.

(d) 0.66 g of 1-[[p-(dimethylamino)benzylidene]-amino]-2,3-dimethylimidazolium tetrafluoroborate, 0.45 g of p-(dimethylamino)benzaldehyde and 0.34 g of piperidine are suspended in 30 ml of toluene, whereupon the suspension is heated to boiling under reflux for about 70 hours on a water separator filled with toluene which contains 5% piperidine. The precipitated material is removed by filtration under suction, washed with toluene, twice with diethyl ether and twice with water and recrystallized from methanol. There is obtained colorless 1-[[p-(dimethylamino)benzylidene]amino]-2-[p-(dimethylamino)styryl]-3-methylimidazolium tetrafluoroborate of melting point 235°–238°.

EXAMPLE 3

(a) A solution of 1-(benzylideneamino)-2-methylimidazole in 1.5N hydrochloric acid is subjected to a steam distillation until benzaldehyde no longer results. The mixture is evaporated and the product obtained is recrystallized from ethanol/ether. There is obtained 1-amino-2-methylimidazole hydrochloride of melting point 124°.

(b) 1.3 g of 1-amino-2-methylimidazole hydrochloride and 2.2 g of p-(dimethylamino)benzaldehyde are stirred at room temperature for 16 hours in 100 ml of glacial acetic acid. The mixture is evaporated, whereupon the residue is treated four times with ethanol and again evaporated each time. The crystalline residue is washed with ether and then treated with saturated sodium hydrogen carbonate solution. The mixture is extracted with methylene chloride, the extract is dried over sodium sulfate and evaporated, and the material obtained is recrystallized from methylene chloride/petroleum ether. There is obtained 1-[[p-(dimethylamino)-benzylidene]amino]-2-methylimidazole of melting point 166°–167°.

(c) 1.37 g of 1-[[p-(dimethylamino)benzylidene]-amino]-2-methylimidazole are dissolved in 15 ml of absolute dimethylformamide. After the addition of 1.57 g of 3,4,5-trimethoxybenzyl bromide the mixture is stirred at room temperature overnight. After cooling the reaction mixture in an ice-bath, the resulting percipicate is removed by filtration under suction, washed twice with ice-cold dimethylformamide and three times with diethyl ether and recrystallized from acetonitrile. There is obtained pale yellow 1-[[p-(dimethylamino)-benzylidene]-amino]-3-(3,4,5-trimethoxy)benzyl-2-methylimidazolium bromide of melting point 238°–241°.

(d) 1.96 g of 1-[[p-(dimethylamino)benzylidene]-amino]-3-(3,4,5-trimethoxy)benzyl-2-methylimidazolium bromide, 0.9 g of p-(dimethylamino)benzaldehyde and 0.7 g of piperidine are suspended in 50 ml of toluene, whereupon the suspension is heated to boiling under reflux for about 60 hours on a water separator (filled with toluene which contains 5% piperidine). The precipitated material is removed by filtration under suction, washed with toluene, twice with diethyl ether and thereafter three times with water and then recrystallized from ethanol and methanol. There is obtained orange colored 1-[[p-(dimethylamino) benzylidene]amino]-2-[p-(dimethylamino)styryl]-3-(3,4,5-trimethoxybenzyl)imidazolium bromide of melting point 253°–256° (decomposition).

EXAMPLE 4

(a) 680 mg of imidazole are suspended in a mixture of 4 ml of absolute N-methyl-2-pyrrolidone and 1 ml of absolute tetrahydrofuran. The suspension is cooled to −40°. While stirring, there is slowly added dropwise thereto within 30 minutes a solution of 4.8 g of 0-(2,4-dinitrophenyl) hydroxylamine in 8 ml of absolute N-methyl-2-pyrrolidone. The reaction mixture is left to stand at 20° for 18 hours, treated with 25 ml of water and 12 ml of 2N hydrochloric acid and extracted five times with 20 ml of ether each time. The acidic solution is stirred with active carbon for 15 minutes and there upon filtered. After the addition of 3 ml of benzaldehyde, 5 ml of 2N hydrochloric acid and 30 ml of ether the mixture is stirred for three hours while cooling with ice. The separated precipitate is removed by filtration and washed twice with water and once with ether. The thus-obtained crude product is re-precipitated from methanol/ether. There is obtained 1,3-bis(benzylideneamino)imidazolium chloride of melting point 193°–196°.

(b) 3.11 g of 1,3-bis(benzylideneamino)imidazolium chloride, 0.32 g of sulfur and 1.01 g of triethylamine are suspended in 20 ml of absolute pyridine, whereupon the mixture is stirred at room temperature for 15 minutes. The reaction mixture is subsequently heated to boiling under reflux for a half hour. After cooling to room temperature the mixture is treated with 100 ml of water. The resulting precipitate is removed by filtration under suction and washed three times with water and three times with ethanol. There is obtained pale yellow 1,3-bis(benzylideneamino)-1,3-dihydro-2H-imidazole-2-thione of melting point 215°–218°.

(c) 3.06 g of 1,3-bis(benzylideneamino)-1,3-dihydro-2H-imidazole-2-thione in 100 ml of absolute dichloromethane are treated with 1.47 g of trimethyloxonium tetrafluoroborate, the mixture is stirred at room temperature for 3 hours and the resulting precipitate is removed by filtration under suction. From the filtrate, there is precipitated by the addition of diethyl ether an additional portion of the desired product which, together with the first portion, is washed once with water, once with cold methanol and three times with diethyl ether and subsequently re-precipitated from acetonitrile/diethyl ether. There is obtained colorless 1,3-bis(benzylideneamino)-2-(methylthio)imidazolium tetrafluoroborate of melting point 215°-220° (decomposition).

(d) 4.47 g of 1,3-bis(benzylideneamino)-2-(methylthio) imidazolium tetrafluoroborate are suspended in 100 ml of water. The suspension is treated with 3.5 ml of 50 percent tetrafluoroboric acid and steam-distilled until benzaldehyde no longer evolves. The colorless, acidic solution, cooled to room temperature, is treated with 2.98 g of p-dimethylaminobenzaldehyde and stirred at room temperature for 3 hours. The resulting yellow precipitate is removed by filtration under suction, washed three times with water, three times with ethanol and twice with diethyl ether and subsequently re-precipitated from acetonitrile/diethyl ether. After recrystallization from ethanol, there is obtained 1,3-bis[[p-(dimethylamino)-benzylidene]amino]-2-(methylthio) imidazolium tetrafluoroborate as a yellow solid of melting point 250°-253° (decomposition).

EXAMPLE 5

Gaseous dimethylamine is passed through a mixture of 2.47 g of 1,3-bis[[p-(dimethylamino)benzylidene]amino]-2(methylthio)imidazolium tetrafluoroborate and 30 ml of absolute dimethylformamide until a weight increase of 0.4 g (corresponding to 1.8 equivalents) is achieved and the mixture is subsequently stirred at room temperature overnight. From the resulting reddish solution, there is obtained by the addition of diethyl ether a crystalline precipitate which is removed by filtration under suction and washed twice with water and ethanol each time. After re-precipitation from dimethylformamide/diethyl ether, there is obtained 1,3-bis[[p-(dimethylamino)benzylidene]amino]-2-(dimethylamino)imidazolium tetrafluoroborate as a yellow solid of melting point 248°-252° (decomposition).

EXAMPLE 6

(a) 1.45 g of absolute morpholine are added under an argon atmosphere to 4.1 g of 1,3-bis-(benzylideneamino)-2-(methylthio)imidazolium tetrafluoroborate in 15 ml of absolute dimethylformamide, whereby the evolution of methyl mercaptan occurs immediately and a yellow-orange solution results. The solution is stirred at room temperature until the cleavage of methyl mercaptan is complete (about 12 hours). Then the solution is treated with 120 ml of diethyl ether and the resulting, slightly yellowish precipitate is removed by filtration under suction. The precipitate is washed five times with diethyl ether, and twice with a small amount of cold ethanol and re-precipitated from acetonitrile/diethyl ether. There is obtained colorless 1,3-bis(benzylideneamino)-2-morpholinoimidazolium tetrafluoroborate of melting point 242°-245° (decomposition).

(b) 2.24 g of 1,3-bis(benzylideneamino)-2-morpholinoimidazolium tetrafluoroborate are suspended in water, whereupon the suspension is treated with 2 ml of 50 percent tetrafluoroboric acid and steam-distilled until benzaldehyde no longer evolves. The colorless, acidic solution obtained is treated with 1.5 g of p-(dimethylamino)benzaldehyde and stirred at room temperature for 3 hours. The resulting orange-yellow precipitate is removed by filtration under suction, washed three times with water, three times with ethanol and three times with diethyl ether and subsequently re-precipitated from dimethylformamide/diethyl ether. There is obtained yellow 1,3-bis[[p-(dimethylamino)-benzylidene]amino]-2-morpholinoimidazolium tetrafluoroborate of melting point 275°-280° (decomposition).

EXAMPLE 7

2.47 g of 1,3-bis[[p-(dimethylamino)benzylidene]amino]-2-(methylthio)imidazolium tetrafluoroborate are suspended in 50 ml of absolute acetonitrile, whereupon the suspension is treated with 7.8 g of absolute 2-amino-5-(diethylamino)pentane. The mixture is stirred at room temperature under an argon atmosphere for about 24 hours. The insoluble constituents are removed by filtration and the filtrate is treated with 450 ml of diethyl ether. The pale yellow precipitate obtained is removed by filtration under suction, washed three times with diethyl ether and recrystallized from methanol/diethyl ether. There is obtained pale yellow 1,3-bis[[p-(dimethylamino) benzylidene]amino]-2-[[4-(diethylamino)-1-methylbutyl]amino]imidazolium tetrafluoroborate of melting point 187°-191° (decomposition).

EXAMPLE 8

0.99 g of 1,3-bis[[p-(dimethylamino)benzylidene]amino]-2-(methylthio)imidazolium tetrafluoroborate is dissolved in 15 ml of absolute dimethylformamide. Dry ammonia is conducted into the reaction solution at room temperature while stirring until the cleavage of methyl mercaptan is complete. The solution is treated with diethyl ether. The precipitate obtained is washed twice with water and twice with cold methanol and re-precipitated from dimethylformamide/diethyl ether. There is obtained yellow 2-amino-1,3-bis[[p-(dimethylamino)benzylidene]amino]imidazolium tetrafluoroborate with a decomposition point >260°.

EXAMPLE 9

(a) 0.18 g of sodium hydride (55 percent dispersion in oil) is washed with tetrahydrofuran. A solution of 0.34 g of 2-(4-methoxyphenyl)-imidazole in 8.3 ml of N-methylpyrrolidone is added dropwise while stirring at 0°. As soon as hydrogen no longer forms the mixture is warmed to room temperature. 0.46 g of O-diphenylphosphinylhydroxylamine is added in three portions. After stirring at room temperature for 18 hours, 8 ml of water are added. The mixture is stirred for an additional 1 hour and extracted six times with 20 ml of dichloromethane each time. The extracts are dried over sodium sulfate and evaporated, whereby the N-methyl-pyrrolidone is removed in a high vacuum. The crude product is chromatographed on 5 g of silica gel while eluting with chloroform/ethanol. There is obtained 1-amino-2-(4-methoxyphenyl)imidazole as a dark colored oil.

(b) 0.1 g of 1-amino-2-(4-methoxyphenyl)imidazole is dissolved in 10 ml of dichloromethane. The solution is treated portionwise during 8 days with 0.29 g of O-diphenylphosphinylhydroxylamine, evaporated and the residue is suspended in 10 ml of water. The difficulty soluble diphenylphosphinic acid is removed by filtration and the filtrate is placed on a column loaded with Amberlite IRA 400 (chloride), whereupon the column is eluted with water. There is obtained 1,3-diamino-2-(4-methoxyphenyl)imidazolium chloride.

(c) 131 mg of 4-(dimethylamino)benzaldehyde are added to a solution of 90 mg of 1,3-diamino-2-(4-methoxyphenyl) imidazolium chloride in 2 ml of glacial acetic acid. After stirring at room temperature for 48 hours, the dark yellow solution is evaporated. The residue is placed on a column loaded with 8 g of silica gel, whereupon the product is eluted with dichloromethane/ethanol (9:1) and recrystallized from ethanol/ether. There is obtained 1,3-bis[[p-(dimethylamino)benzylidene]amino]-2-(p-methoxyphenyl)imidazolium chloride of melting point 250°.

EXAMPLE 10

(a) 3.55 g of sodium hydride (55 percent dispersion in oil) are washed with tetrahydrofuran. A solution of 6.5 g of 2-(4-methoxyphenyl)-imidazole in 153 ml of N-methylpyrrolidone is added dropwise thereto at 0°. As soon as hydrogen no longer forms a total of 8.8 g of O-diphenylphosphinylhydroxylamine are added portionwise thereto at room temperature. After stirring for 18 hours, the mixture is treated with 150 ml of water, acidified with 80 ml of 2N hydrochloric acid, stirred at 0° for an additional 1 hour and the precipitated diphenylphosphinic acid is removed by filtration. Then, 3.85 ml of benzaldehyde are added to the acidic dark red filtrate and the mixture is stirred for about 20 hours. The dark solution is washed twice with 120 ml of ether each time and adjusted to pH 14 by the addition of 20 ml of 4N sodium hydroxide solution while cooling with ice. The mixture is extracted five times with 150 ml of dichloromethane each time. The extract is dried over sodium sulfate and evaporated, whereby the N-methylpyrrolidone is removed in a high vacuum. The residue is placed on a column loaded with 200 g of silica gel and the product is eluted with dichloromethane/ethanol (98:2) and then crystallized from ethanol. There is obtained 1-(benzylideneamino)-2-(p-methoxyphenyl)imidazole of melting point 155°.

(b) 3.73 g of 1-bromo-3,3-dimethyl-2-butanone are added to a solution of 4.6 g of 1-(benzylideneamino)-2-(p-methoxyphenyl)imidazole in 250 ml of absolute acetonitrile. After stirring at 60° for 24 hours, the solution is evaporated and the residue is crystallized from ethanol/ether. There is obtained 1-(benzylideneamino)-2-(p-methoxyphenyl)-3-(pivaloylmethyl)imidazolium bromide of melting point 244°.

(c) 5.0 g of 1-(benzylideneamino)-2-(p-methoxyphenyl)-3-(pivaloylmethyl)imidazolium bromide are suspended in 300 ml of water. The suspension is then treated with 10 ml of 48 percent hydrobromic acid. The suspension is now subjected to a steam distillation until benzaldehyde no longer results. The solution is evaporated. The residue is treated with ethanol and the solvent is removed by distillation. There is obtained 1-amino-2-(p-methoxyphenyl)-3-(pivaloylmethyl)imidazolium bromide as an oil.

(d) 1.50 g of p-(dimethylamino)benzaldehyde are added to a solution of 3.7 g of 1-amino-2-(p-methoxyphenyl)-3-(pivaloylmethyl)imidazolium bromide in 25 ml of glacial acetic acid. The mixture is stirred at room temperature for 15 hours. Then, 20 ml of ether are added thereto and, after an additional 3 hours, the product is removed by filtration. After recrystallization from ethanol/ether, there is obtained 1-[[p-(dimethylamino)benzylidene]amino]-2-(p-methoxyphenyl)-3-(pivaloylmethyl)imidazolium bromide of melting point 241°.

EXAMPLE 11

(a) 9.0 g of sodium hydride (55 percent dispersion in oil) are suspended in 600 ml of absolute tetrahydrofuran. 8.5 g of 2-(p-methoxyphenyl)imidazole are added thereto within 5 minutes. The mixture is stirred until hydrogen is no longer liberated (1 hour). Then, 34.5 g of O-diphenylphosphinylhydroxylamine are added portionwise thereto at 10° and the mixture is stirred at 10° for an additional 40 minutes and then at room temperature for 18 hours. Saturated sodium chloride solution is added thereto at 5° and the mixture is subsequently extracted with methylene chloride/methanol (99.5:0.5). The extract is dried over sodium sulfate and evaporated. There is obtained 1-amino-2-(p-methoxyphenyl)imidazole as a brown oil.

(b) 9 g of 1-amino-2-(p-methoxyphenyl)imidazole are dissolved in 300 ml of glacial acetic acid, whereupon the solution is treated with 21.3 g of p-(dimethylamino)benzaldehyde. After 24 hours, the mixture is evaporated and the residue is placed on a column loaded with 300 g of silica gel. The product is eluted with dichloromethane/methanol (95:5). The dark eluate is treated with active carbon and evaporated. The product is crystallized twice from methylene chloride/petroleum ether. There is obtained 1-[[p-(dimethylamino)benzylidene]amino]-2-p-methoxyphenyl)imidazolium acetate of melting point 93°. The resulting salt is treated with aqueous sodium bicarbonate solution and extracted with dichloromethane. The extract is dried over sodium sulfate and evaporated. The product is crystallized from petroleum ether. There is obtained 1-[[p-(dimethylamino)benzylidene]amino]-2-(p-methoxyphenyl)imidazole of melting point 108°.

In an analogous manner:

From 2-(p-tolyl)imidazole, there is obtained 1-[[p-(dimethylamino)benzylidene]amino]-2-(p-tolyl)imidazole of melting point 127°–128° and from 2-[(p-methylthio)phenyl]imidazole there is obtained 1-[[p-(dimethylamino)benzylidene]amino]-2-[p-(methylthio)phenyl]imidazole of melting point 147°.

(c) In analogy to Example 11b), from 1-amino-2-(p-methoxyphenyl)imidazole and 4-(dimethylamino)-3,5-dimethoxybenzaldehyde, there is obtained 1-[[4-(dimethylamino)-3,5-dimethoxybenzylidene]amino]-2-(p-methoxyphenyl)imidazole of melting point 118°–119° (ether/petroleum ether).

(d) 0.45 g of sodium hydride (55 percent dispersion in oil) is washed with absolute tetrahydrofuran. A solution of 1.02 g of 2-(3,4-dimethoxyphenyl)imidazole in 50 ml of N-methylpyrrolidone is then added dropwise thereto. The mixture is stirred at room temperature for 20 minutes. 2.33 g of O-diphenylphosphinylhydroxylamine are added thereto at 0° and the mixture is shaken. After standing for 24 hours, water is added thereto and the mixture is extracted with methylene chloride. The extract is dried over sodium sulfate and evaporated. The residual oil (1-amino-2-(3,4-dimethoxyphenyl)imidazole) is dissolved in 20 ml of glacial acetic acid. Then. 1.49 g of p-(dimethylamino)benzaldehyde are added thereto. The mixture is left to stand at room temperature for 2 days and evaporated. The crude product is placed on a column loaded with 100 g of silica gel. The product is eluted with methylene chloride/methanol (19:1). The eluate is treated with sodium bicarbonate solution and extracted with methylene chloride. The extract is dried over sodium sulfate and evaporated. After crystallization from ether/petroleum ether, there is obtained 1-[[p-(dimethylamino)benzylidene]amino]-2-(3,4-dimethoxyphenyl)imidazole of melting point 149°.

In an analogous manner:

From 2-phenylimidazole, there is obtained 1-[[p-(dimethylamino)benzylidene]amino]-2-phenylimidazole of melting point 137°;

from 2-(p-ethoxyphenyl)imidazole, there is obtained 1-[[p-(dimethylamino)benzylidene]amino]-2-(pethoxyphenyl)imidazole of melting point 168°–169°;

from 2-(m-methoxyphenyl)imidazole, there is obtained 1-[[p-(dimethylamino)benzylidene]amino]-2-(m-methoxyphenyl)imidazole of melting point 131°–133° (methylene chloride/petroleum ether);

from 2-(3,4,5-trimethoxyphenyl)imidazole, there is obtained 1-[[p-(dimethylamino)benzylidene]amino]-2-(3,4,5-trimethoxyphenyl)imidazole of melting point 163° (ethanol) and from 2-(p-nitrophenyl)imidazole, there is obtained 1-[[p-(dimethylamino)benzylidene]amino]-2-p-nitrophenyl)imidazole of melting point 200° (ethanol/ether).

(e) A solution of 160 mg of 1-[[p-(dimethylamino)benzylidene]amino]-2-(p-methoxyphenyl)imidazole and 400 mg of 1-bromo-3,3-dimethyl-2-butanone in 3 ml of acetonitrile is stirred at 60° for 20 hours. The product is removed by filtration and washed with ether. There is obtained 1-[[p-(dimethylamino)benzylidene]amino]-2-(p-methoxyphenyl)-3-(pivaloylmethyl)imidazolium bromide of melting point 262°.

In an analogous manner:

(f) From 1-[[p-(dimethylamino)benzylidene]amino]-2-phenylimidazole and 1-bromo-3,3-dimethyl-2-butanone, there is obtained after 2 days at 60°, 3-[[p-(dimethylamino)benzylidene]amino]-2-phenyl-1-(pivaloylmethyl)imidazolium bromide of melting point 245°;

(g) from 1-[[p-(dimethylamino)benzylidene]amino]-2-(p-tolyl)imidazole and 1-bromo-3,3-dimethyl-2-butanone, there is obtained after 20 hours at 60°, 3-[[p-(dimethylamino)benzylidene]amino]-1-(pivaloylmethyl)-2-(p-tolyl)imidazolium bromide of melting point 260°;

(h) from 1-[[p-(dimethylamino)benzylidene]amino]-2-(3,4-dimethoxyphenyl)imidazole and 1-bromo-3,3-dimethyl-2-butanone, there is obtained after 20 hours at 60° 3-[[p-(dimethylamino)benzylidene]amino]-2-(3,4-dimethoxyphenyl)-1-(pivaloylmethyl)imidazolium bromide of melting point 270°–271°;

(i) from 1-[[p-(dimethylamino)benzylidene]amino]-2-[p-(methylthio)phenyl]imidazole and 1-bromo-3,3-dimethyl-2-butanone, there is obtained after 4 days at 60°, 3-[[p-(di-methylamino)benzylidene]amino]-2-[p-(methylthio)phenyl]-1-(pivaloylmethyl)imidazolium bromide of melting point 255°;

(j) from 1-[[p-(dimethylamino)benzylidene]amino]-2-(p-ethoxyphenyl)imidazole and 1-bromo-3,3-dimethyl-2-butanone, there is obtained after 4 days at 60°, 3-[[p-(dimethylamino)benzylidene]amino]-2-(p-ethoxyphenyl)-1 -(pivaloylmethyl)imidazolium bromide of melting point 242°;

(k) from 1-[[p-(dimethylamino)benzylidene]amino]-2-(3,4,5-trimethoxyphenyl)imidazole and 1-bromo-3,3-dimethyl-2-butanone, there is obtained 3-[[p-(dimethylamino)benzylidene]amino]-2-(3,4,5trimethoxphenyl)-1-(pivaloylmethyl)imidazolium bromide of melting point 224° (ethanol/ether);

(l) from 1-[[p-(dimethylamino)benzylidene]amino]-2-(m-methoxyphenyl)imidazole and 1-bromo-3,3-dimethyl-2-butanone, there is obtained 3-[[p-(dimethylamino)benzylidene]amino]-2-(m-methoxyphenyl)-1-(pivaloylmethyl)imidazolium bromide of melting point 238° (methylene chloride/methanol/petroleum ether; decomposition);

(m) from 1-[[p-(dimethylamino)benzylidene]amino]-2-(p-nitrophenyl)imidazole and 1-bromo-3,3-dimethyl-2-butanone, there is obtained 3-[[p-(dimethylamino)benzylidene]amino]-2-(p-nitrophenyl)-1-(pivaloylmethyl)imidazolium bromide of melting point 258° (ethanol/ether/hexane) and (n) from 1-[[4-(dimethylamino)-3,5-dimethoxybenzylidene]amino]-2-(p-methoxyphenyl)imidazole and 1-bromo-3,3-dimethyl-2-butanone, there is obtained after 15 days at room temperature 3-[[4-(dimethylamino)-3,5-dimethoxybenzylidene]amino]-2-(p-methoxyphenyl)-1-(pivaloylmethyl)imidazolium bromide of melting point 218°–220° (acetonitrile/ether).

EXAMPLE 12

(a) 0.60 g of p-(dimethylamino)phenacyl bromide is added to a solution of 0.80 g of 1-[[p-(dimethylamino)benzylidene]amino]-2-(p-methoxyphenyl)-imidazole in 80 ml of acetonitrile. After stirring at room temperature for 3 days, the product is removed by filtration and washed with ether. There is obtained 3-[[p-(dimethylamino)benzylidene]amino]-1-[p-(dimethylamino)phenacyl]-2-(p-methoxyphenyl)imidazolium bromide of melting point 234°.

(b) In an analogous manner, from 1-[[p-(dimethylamino)benzylidene]amino]-2-(3,4,5-trimethoxyphenyl)imidazole, there is obtained after 2 days at 50° in acetonitrile 3-[[p-(dimethylamino)benzylidene]amino]-1-[p-(dimethylamino)phenacyl]-2-(3,4,5-trimethoxyphenyl)imidazolium bromide of melting point 232° (ethanol/ether).

EXAMPLE 13

0.92 g of p-methoxyphenacyl bromide is added to a solution of 0.32 g of 1-[[p-(dimethylamino)-benzylidene]amino]-2-(p-methoxyphenyl)imidazole in 20 ml of 2-propanol. After stirring for 3 days with the exclusion of light, the mixture is evaporated. The residue is placed on a column loaded with 20 g of silica gel. The product is eluted with methylene chloride/methanol (9:1). After crystallization from ethanol/ether, there is obtained 3-[[p-(dimethylamino)benzylidene]amino]-2-(p-methoxyphenyl)-1-(p-methoxyphenacyl)imidazolium bromide of melting point 188°–191°.

EXAMPLE 14

(a) 0.93 g of p-chlorophenacyl bromide is added to a solution of 0.64 g of 1-[[p-(dimethylamino)benzylidene]amino]-2-(p-methoxyphenyl)imidazole in 20 ml of acetonitrile. After stirring at 60° for 6 hours, the mixture is left to stand for 16 hours and the product is removed by filtration and washed with ether. There is obtained 1-(p-chlorophenacyl)-3-[[p-(dimethylamino)benzylidene]amino]-2-(p-methoxyphenyl)imidazolium bromide of melting point 242°.

In an analogous manner, from 1-[[p-(dimethylamino)benzylidene]amino]-2-(p-methoxyphenyl)imidazole and:

(b) p-nitrophenacyl bromide, there is obtained after 3 days at room temperature, 3-[[p-(dimethylamino)benzylidene]-amino]-2-(p-methoxyphenyl)-1-(p-nitrophenacyl)imidazolium bromide of melting point 232°;

(c) ethyl 2-bromoacetate, there is obtained after 2 days at 50°, 1-[[p-(dimethylamino)benzylidene]amino]-3-((ethoxycarbonyl)methyl]-2-(p-methoxyphenyl)imidazolium bromide of melting point 165°–167°;

(d) 3,4,5-trimethoxybenzyl chloride, there is obtained after 2 days at 60°, 3-[[p-(dimethylamino)benzylidene]amino]-2-(p-methoxyphenyl)-1-(3,4,5-trimethoxybenzyl)imidazolium chloride of melting point 227°–228° (ethanol/ether);

(e) t-butyl 2-bromoacetate, there is obtained after 2 days at room temperature, 1-[(t-butoxycarbonyl)methyl]-3-[[p-(dimethylamino)benzylidene]amino]-2-(p-methoxyphenyl)imidazolium bromide of melting point 203° (acetonitrile).

EXAMPLE 15

(a) 2.05 g of 1,3-bis[[p-(dimethylamino)benzylidene]amino]-2-methylimidazolium chloride and 7.35 g of N,N-dimethylformamide diethyl acetal are stirred at 100° for 45 minutes in 150 ml of 1-propanol. The product is precipitated by the addition of ether. The precipitate is crystallized from dichloromethane/methanol and recrystallized from ethanol. There is obtained 1,3-bis[[p-(dimethylamino)benzylidene]amino]-2-[2-(dimethylamino)vinyl]imidazolium chloride of melting point 246°–248°.

In an analogous manner, from 1,3-bis[[p-(dimethylamino)benzylidene]amino]-2-methylimidazolium chloride and:

(b) Tetrahydro-4H-1,4-thiazine-4-carboxaldehyde diethyl acetal, there is obtained after 7 days at 55° in dimethylformamide, 1,3-bis[[p-(dimethylamino)benzylidene]amino]-2-(tetrahydro-4H-1,4-thiazin-4-yl)vinyl]imidazolium chloride of melting point 247° (decomposition);

(c) cis-2,6-dimethylmorpholine-4-carboxaldehyde diethyl acetal, there is obtained after 6 days at 50° in dimethylformamide, 1,3-bis[[p-(dimethylamino)benzylidene]amino]-2-[2-(cis-2,6-dimethylmorpholino)vinyl]imidazolium chloride of melting point 251° (decomposition);

(d) pyrrolidine-1-carboxaldehyde diethyl acetal there is obtained after 24 hours at reflux temperature in methylene chloride, 1,3-bis[[p-(dimethylamino)benzylidene]amino]-2-[2-(1-pyrrolidinyl)vinyl]imidazolium chloride of melting point 260° (decomposition);

(e) morpholine-4-carboxaldehyde diethyl acetal, there is obtained after 4 days at reflux temperature in methylene chloride, 1,3-bis[[p-(dimethylamino)benzylidene]amino]-2-(2-morpholinovinyl)imidazolium chloride of melting point 259°–260° (decomposition);

(f) piperidine-1-carboxaldehyde diethyl acetal, there is obtained after 4 days at reflux temperature in methylene chloride, 1,3-bis[[p-(dimethylamino)benzylidene]amino]-2-(2-piperidinovinyl)imidazolium chloride of melting point 240° (decomposition);

(g) 4-methylpiperazine-1-carboxaldehyde diethyl acetal, there is obtained after 6 days at 60° in dimethylformamide, 1,3-bis[[p-(dimethylamino)benzylidene]amino]2-[2-(4-methyl-1-piperazinyl)vinyl]imidazolium chloride of melting point 256°–258° (decomposition).

EXAMPLE 16

(a) In analogy to Example 1c, from 1,3-diamino-2-methylimidazolium chloride and 2,6-dimethyl-4-(dimethylamino)benzaldehyde, there is obtained 1,3-bis[[4-(dimethylamino)2,6-dimethylbenzylidene]amino]-2-methylimidazolium chloride of melting point 216°.

(b) In analogy to Example 15(a), from 1,3-bis[[4-(dimethylamino)-2,6-dimethylbenzylidene]amino]-2-methylimidazolium chloride and N,N-dimethylformamide diethyl acetal, there is obtained after 4 hours at room temperature in 1-propanol, 1,3-bis[[4-(dimethylamino)-2,6-dimethylbenzylidene]-amino]-2-[2-dimethylamino)vinyl]imidazolium chloride of melting point 230°–235° (decomposition):

EXAMPLE 17

73.5 g of N,N-dimethylformamide diethyl acetal are added to 20.5 g of 1,3-bis[[p-(dimethylamino)benzylidene]amino]-2-methylimidazolium chloride in 400 ml of dry dimethylformamide. After stirring at 50° for 4 days, the mixture is left to cool. Then, 250 ml of ether are added thereto and the product is removed by filtration and is recrystallized from dry ethanol. There is obtained 1,3-bis[[p-(dimethylamino) benzylidene]amino]-2-[2-(dimethylamino)vinyl]imidazolium chloride of melting point 265° (decomposition).

EXAMPLE 18

(a) 32.8 g of sodium hydride (55 percent dispersion in oil) are washed with absolute tetrahydrofuran. A solution of 53.1 g of 2-phenylimidazole in 1500 ml of N-methylpyrrolidone is then added dropwise thereto at 0°. The mixture is stirred at 0° for a half hour and at room temperature for about 1.5 hours (until gas evolution is no longer to be observed). Then, 85 g of O-diphenylphosphinylhydroxylamine are added thereto. The mixture is stirred at room temperature for 20 hours and subsequently 910 ml of water are added thereto. The dark solution is stirred at room temperature for 1 hour and then extracted seven times with 300 ml of dichloromethane each time. The extract is dried over sodium sulfate and evaporated. The residual oil is placed on a column loaded with 900 g of silica gel, whereupon the 1-amino-2-phenylimidazole is eluted with dichloromethane/ethanol (85:15).

In an analogous manner, from 2-(p-chlorophenyl)imidazole, there is obtained 1-amino-2-(p-chlorophenyl)imidazole of melting point 160° (ethanol/petroleum ether).

(b) 43.8 g of O-diphenylphosphinylhydroxylamine are added to 30.1 g of 1-amino-2-phenylimidazole in 2000 ml of dichloromethane. After stirring at room temperature for 3 days an additional 21.9 g of O-diphenylphosphinylhydroxylamine are added. After one day, the mixture is filtered and the filter material is washed four times with 150 ml of dichloromethane each time. The residue is placed on a column loaded with 700 ml of ion-exchanger Amberlite IRA 400 (chloride), whereupon elution is carried out with water. The eluate is evaporated and the residue is treated with ethanol and evaporated. After drying in a high vacuum over potassium hydroxide, there is obtained 1,3-diamino-2-phenylimidazolium chloride.

In an analogous manner, from 1-amino-2-(p-chlorophenyl)imidazole there is obtained 1,3-diamino-2-(p-chlorophenyl)imidazolium chloride of melting point 210° (ethanol/ether; containing 7% ammonium chloride and 1% water).

(c) 0.45 g of 1,3-diamino-2-phenylimidazolium chloride is dissolved in 6 ml of glacial acetic acid. 0.64 g of 4-dimethylaminobenzaldehyde are added thereto. After stirring for 24 hours, about 1 ml of absolute ether is added thereto. One day later the mixture is evaporated and the residue is placed on a column loaded with 25 g of silica gel. After elution with dichloromethane/ethanol (98:2) and crystallization from ethanol/ether there is obtained 1,3-bis[[p-(dimethylamino)benzylidene]amino]-2-phenylimidazolium chloride of melting point 242°.

(d) In an analogous manner, from 1,3-diamino-2-(p-chlorophenyl)imidazolium chloride there is obtained 2-(p-chlorophenyl)-1,3-bis[[p-(dimethylamino)benzylidene]amino]imidazolium chloride of melting point 242° (decomposition).

EXAMPLE 19

(a) 0.88 g of sodium hydride (55 percent dispersion in oil) is washed with tetrahydrofuran. A solution of 1.72 g of 2-(2-phenylethyl)imidazole in 50 ml of N-methylpyrrolidone is then added dropwise thereto at 0°. The mixture is stirred at room temperature until gas evolution is no longer to be observed. Then, 4.66 g of O-diphenylphosphinylhydroxylamine are added thereto. After stirring for 18 hours, 25 ml of water are added dropwise thereto, whereupon the mixture is stirred at room temperature for an additional 1 hour. After the addition of 2 g of sodium chloride, the mixture is extracted with dichloromethane. The extract is dried over sodium sulfate and evaporated. The residue is taken up in methylene chloride/methanol/ether, whereupon the mixture is filtered and evaporated. There is obtained an oil which contains 1-amino-2-(2-phenylethyl)imidazole.

(b) This oil (2.7 g) is treated with 50 ml of glacial acetic acid and 2.98 g of p-dimethylaminobenzaldehyde. After standing at room temperature for 18 hours, the reaction solution is evaporated. The residue is placed on a column loaded with 200 g of silica gel. The product is eluted with methyl acetate and crystallized from dichloromethane/methanol/petroleum ether. There is obtained 1-[[p-(dimethylamino)benzylidene]amino]-2-(phenylethyl)imidazole of melting point 153°–154°.

(c) 8.0 g of 1-bromo-3,3-dimethyl-butan-2-one are added to 0.64 g of 1-[[p-(dimethylamino)-benzylidene]amino]-2-(phenylethyl)imidazole in 60 ml of acetonitrile. After stirring for 24 hours, the product is removed by filtration. There is obtained 3-[p-(dimethylamino)benzylidene]amino]-2-(phenylethyl)-1-(pivaloylmethyl)imidazolium bromide of melting point 231°.

EXAMPLE A 1,3-Bis[[(p-dimethylamino)benzylidene]amino]-2-[2-(dimethylamino)vinyl]imidazolium chloride is used in a known manner as the active substance for the preparation of tablets of the following composition:

|  | mg/tablet |
| --- | --- |
| Active substance | 100 |
| Lactose | 192 |
| Maize starch | 80 |
| Hydrolyzed maize starch | 20 |
| Calcium stearate | 8 |
| Tablet weight | 400 mg |

The compounds listed hereinafter can also be used as the active substance:
1,3-Bis[[(p-dimethylamino)benzylidene]amino]-2-(2-piperidinovinyl)imidazolium chloride;
1,3-bis[[(p-dimethylamino)benzylidene]amino]-2-(2-morpholinovinyl)imidazolium chloride;
1,3-bis[[(p-dimethylamino)benzylidene]amino-2-phenylimidazolium chloride;
1,3-bis[[(p-dimethylamino)benzylidene]amino-2-(p-chlorophenyl)imidazolium chloride;
3-[[p-(dimethylamino)benzylidene]amino]-1-(pivaloylmethyl)-2-(p-tolyl)imidazolium bromide; and
3-[[p-(dimethylamino)benzylidene]amino]-1-(pivaloylmethyl)-2-(m-methoxyphenyl)imidazolium bromide.

We claim:
1. A compound of the formula

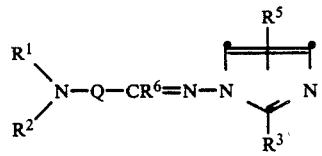

V wherein Q is a carbo mono- or bicyclic aromatic group with two free valences which may be unsubstituted or substituted by one or two substituents selected from the group consisting of lower alkyl, lower alkoxy, lower alkylthio, lower alkanoyl, lower alkoxycarbonyl, phenyl, halogen, trifluoromethyl, hydroxy, nitro and cyano, the group —NR$^1$R$^2$ is a basic amino group represented by the formula —NRR' in which R is hydrogen or lower alkyl and R' is a saturated lower hydrocarbon group which is unsubstituted or substituted by one or two lower alkoxy or hydroxy groups or by an amino, lower alkylamino, lower dialkyamino, oxo, lower alkoxycarbonyl or lower alkylenedioxy group, R$^3$ is lower alkylthio, lower alkoxy or the group —(A)$_n$—Ra, n is the integer 0 or 1, A is vinylene or lower alkylene, Ra is a carbo mono- or bicyclic aromatic group which may be unsubstituted or substituted by one, two or three substituents selected from the group consisting of di(lower alkyl)amino, lower alkyl, lower alkoxy, lower alkylthio, lower alkanoyl, lower alkoxycarbonyl, phenyl, halogen, hydroxy, trifluoromethyl, nitro and cyano, or a basic amino group represented by the formula —NRR' in which R is hydrogen or lower alkyl and R' is a saturated lower hydrocarbon group which is unsubstituted or substituted by one or two lower alkoxy or hydroxy groups or by an amino, lower alkylamino, lower dialkyamino, oxo, lower alkoxycarbonyl or lower alkylenedioxy group, R$^5$ is hydrogen, lower alkyl, lower hydroxyalkyl, lower alkoxyalkyl, lower haloalkyl, a carbo mono- or bicyclic aromatic group which may be unsubstituted or substituted by one, two or three substituents selected from the group consisting of di(lower alkyl)amino, lower alkyl, lower alkoxy, lower alkylthio, lower alkanoyl, lower alkoxycarbonyl, phenyl, halogen, hydroxy, trifluoromethyl, nitro and cyano or a fused benzene ring and R$^6$ is hydrogen or lower alkyl.

2. A compound in accordance with claims 1, wherein R$^5$ is hydrogen.

3. A compound in accordance with claim 1, 1-[[p-(dimethylamino)benzylidene]amino]-2-(p-tolyl)imidazole.

* * * * *